(12) United States Patent
Vasudevan et al.

(10) Patent No.: US 8,691,577 B2
(45) Date of Patent: Apr. 8, 2014

(54) **SOMATIC EMBRYOGENESIS OF *JATROPHA CURCAS* FROM OVULES**

(75) Inventors: Ramesh Anbazhagan Vasudevan, Singapore (SG); Srinivasan Ramachandran, Singapore (SG)

(73) Assignee: Joil (S) Pte Ltd., Singapore (SG)

( * ) Notice: Subject to any disclaimer, the term of this patent is extended or adjusted under 35 U.S.C. 154(b) by 550 days.

(21) Appl. No.: 13/054,656

(22) PCT Filed: Jun. 18, 2009

(86) PCT No.: PCT/SG2009/000221
§ 371 (c)(1),
(2), (4) Date: Jan. 18, 2011

(87) PCT Pub. No.: WO2010/011184
PCT Pub. Date: Jan. 28, 2010

(65) Prior Publication Data
US 2011/0117652 A1    May 19, 2011

Related U.S. Application Data

(60) Provisional application No. 61/082,896, filed on Jul. 23, 2008.

(51) Int. Cl.
*C12N 5/00* (2006.01)
*C12N 5/02* (2006.01)

(52) U.S. Cl.
USPC ......................................................... 435/430

(58) Field of Classification Search
USPC ......................................................... 435/430
See application file for complete search history.

(56) References Cited

FOREIGN PATENT DOCUMENTS

| CN | 1799340 A | 7/2006 |
|---|---|---|
| CN | 101138320 A | 3/2008 |

OTHER PUBLICATIONS

Divakara, B.N., H.D. Upadhyaya, S.P. Wani, C.L. Laxmipathi Gowda "Biology and genetic improvement of *Jatropha curcas* L.: A review." Applied Energy 87 (2010) 732-742.*
Greene, David "How a Biofuel Dream Called *Jatropha* Came Crashing Down" The Salt (NPR Radio Show transcript) Aug. 21, 2012 accessed at http://www.npr.org/templates/transcript.php?storyId=159391553 Apr. 2, 2013.*
Anonymous from Wikipedia "*Jatropha curcas*". Accessed at http://en.wikipedia.org/wiki/Jatropha_curcas Apr. 2, 2013.*
Jah, Timir baran, Priyanka Mukherjee, Jukul Manjari Datta. "Somatic embryogenesis in *Jatropha curcas* Linn., an important biofuel plant" Plant Biotechnol Rep (2007) 1: 135-140 Jul. 26, 2007.*
Anonymous. "Mitotic Inhibitor" from Wikipedia accessed at http://en.wikipedia.org/wiki/Mitotic_inhibitor Apr. 2, 2013 pp. 1-4.*
Mukerjee, Priyanka, Alok Varshney, T. Sudhakar Johnson and Timir Baran Jah. "*Jatropha curcas*: a review on biotechnological status and challenges." Plant Biotechnol Rep. (2011) 5: 197-215 Apr. 22, 2011.*
Hawkins, Doug and Yingheng Chen. "*Jatropha* Plant With a Future" Hardman & Co. Nov. 15, 2012 available at www.hardmanandco.com.*
Ceasar, S. A and S. Ignacimuthu. "Applications of biotechnology and biochemical engineering for the improvement of *Jatropha* and Biodiesel: A review." Renewable and Sustainable Energy Reviews 15 (2011) 5176-5185 Sep. 15, 2011.*
Savka et al. "Culture of Ovules Containing Immature Embryos of Eastern Cottonwood in vitro" Hardwood Forest Conference at University of Illinois Apr. 15-17, 1985. pp. 234-239.*
Sujatha, M. et al., "Role of biotechnological interventions in the improvement of castor (*Ricinus communis* L.) and *Jatropha curcas* L.", Biotechnology Advances, May, 22, 2008, 26: 424-435.
Li, M. et al., "Establishment of an Agrobacterium-mediated cotyledon disc transformation method for *Jatropha curcas*", Plant Cell Tiss Organ Cult, (Dec. 2008), 92: 173-181.
Kalimuthu, K. et al., "In vitro Propagation of the Biodiesel Plant *Jatropha curcas* L.", Plant Tissue Cult. & Biotech., (Dec. 2007), 17(2): 137-147.
Soomro, R. et al., "Establishment of Callus and Suspension Culture in *Jatropha curcas*", Pak. J. Bot., (2007). 39(7): 2431-2441.
Jha, T.B. et al., "Somatic embryogenesis in *Jatropha curcas* Linn., an important biofuel plant", Plant Biotechnol Rep, (2007), 1:135-140.
Sujatha, M. et al., "Morphogenic responses of *Jatropha integerrima* explants to cytokinins", Biologia, Bratislava, (2000), 55(1):99-104.
Sardana, J. et al., "An Expeditious Method for Regeneration of Somatic Embryos in *Jatropha curcas* L.", Phytomorphology, (2000), 50(3&4): 239-242.
Puddephat, I.J. et al, "Influence of stock plant pretreatment on gynogenic embryo induction from flower buds of onion," Plant Cell Tissue and Organ Culture, vol. 57, No. 2, 1999, pp. 145-148, XP002665934, 4 pages.
Sato, S. et al., "Production of doubled haploid plants of carnation (*Dianthus caryophyllus* L.) by pseudofertilized ovule culture," Scientia Horticulturae (Amsterdam), vol. 83, No. 3-4, Mar. 31, 2000, pp. 301-310, XP002665935, 10 pages.
Supplementary European Search Report, Reference: HB/P42540EP, Application No./Patent No. 09800627.3-1212/2315518 PCT/SG2009000221, Mail date: Dec. 28, 2011, 6 pages.

* cited by examiner

*Primary Examiner* — Wendy C Haas
(74) *Attorney, Agent, or Firm* — Rothwell, Figg, Ernst & Manbeck P.C.

(57) ABSTRACT

The present invention relates to the field of somatic embryo production, particularly to methods for somatic embryogenesis of *Jatropha* from ovules. More specifically, the present invention relates to a method and media compositions for somatic embryogenesis of *Jatropha curcas* from ovules of unopened flower buds. The method is well suited for *Jatropha curcas* transformation, for producing clonal planting stock useful for large scale *Jatropha curcas* plantation and for producing haploids, double haploids, diploids and disease-free plantlets.

26 Claims, 3 Drawing Sheets

SOMATIC EMBRYOGENESIS OF *JATROPHA CURCAS* FROM OVULES

CROSS-REFERENCE TO RELATED APPLICATIONS

The present application is a national stage filing under 35 U.S.C. §371 of PCT/SG2009/000221, filed on 18 Jun. 2009, and claims the benefit of priority to U.S. Provisional Patent Application Ser. No. 61/082,896, filed 23 Jul. 2008, each application is incorporated herein by reference in its entirety.

BACKGROUND OF THE INVENTION

The present invention relates to the field of somatic embryo production, particularly to methods for somatic embyrogenesis of *Jatropha* from ovules. More specifically, the present invention relates to a method and media compositions for somatic embryogenesis of *Jatropha curcas* from ovules of unopened flower buds. The method is well suited for *Jatropha curcas* transformation, for producing clonal planting stock useful for large scale *Jatropha curcas* plantation and for producing haploids, double haploids, diploids and disease-free plantlets.

The publications and other materials used herein to illuminate the background of the invention or provide additional details respecting the practice, are incorporated by reference, and for convenience are respectively grouped in the Bibliography.

*Jatropha curcas*, belonging to the family of Euphorbiaceous, is a plant of Latin American origin, widely spread throughout the arid and semi-arid tropical regions of the world. *Jatropha* is a large genus comprising over 170 species. The most common species in India are *J. curcas, J. glandulifera, J. gossypifolia, J. multifida, J. nana, J. panduraefolia, J. villosa* and *J. podagrica. J. curcas* is a small tree or shrub with smooth gray bark, which exudes whitish colored, watery, latex when cut. Normally, it grows between three and five meters in height, but can attain a height of up to eight or ten meters under favorable conditions. It is a drought-resistant plant, living up to 50 years and growing on marginal lands.

*J. curcas* has large green to pale green leaves, which are aligned alternate to sub-opposite. The leaves are three-five lobed with a spiral phyllotaxis. The petiole of the flowers ranges between 6-23 mm in length. The flowers are formed in hot seasons. Several crops are formed provided the soil is moisture is good and temperatures are high. In conditions where continuous growth occurs, an imbalance of pistillate or staminate flower production results in a higher number of female flowers. Fruits are produced in winter when the shrub is leafless. Each inflorescence yields a bunch of approximately 10 or more ovoid fruits. Three, bi-valved cocci are formed after the seeds mature and the fleshy exocarp dries. The seeds become mature when the capsule changes from green to yellow, after two to four months from fertilization. The blackish, thin-shelled seeds are oblong and resemble small castor seeds. This plant has various medicinal uses especially in nutraceuticals, pharmaceutical, dermatological, and personal care products. The latex of *Jatropha curcas* has anticancer properties due to the presence of an alkaloid known as "jatrophine." The tender twigs are used for cleaning teeth. The juice of the leaf is used for external application for piles. The roots are used as an antidote for snake-bites. The seeds are used for antihelmithic purposes. The bark yields a dark blue dye used for coloring cloth, fish net and lines. Most of the *Jatropha* species are ornamental except for *J. curcas* and *J. glandulifera* which are oil-yielding species. The seeds of these species contain semi-dry oil which has been found useful for medicinal and veterinary purposes.

The oil content is 25-30% in the seeds and 50-60% in the kernel. The oil contains 21% saturated fatty acids and 79% unsaturated fatty acids. *Jatropha* oil contains linolenic acid (C 18:2) and oleic acid (C18:1) which together account for up to 80% of the oil composition. Palmitic acid (C16:0) and stearic acid (C18:0) are other fatty acids present in this oil. The oil is non-edible, however it has the potential to provide a promising and commercially viable alternative to diesel oil as it has all the desirable physicochemical and performance characteristics as that of diesel. The plant *J. curcas* has lately attracted particular attention as a tropical energy plant. The seed oil can be used as a diesel engine fuel for it has characteristics close to those of fossil fuel diesel. Moreover, due to its non-toxic and biodegradable nature, *Jatropha* biodiesel meets the European EN 14214 standards of a pure and blended automotive fuel for diesel engines. *Jatropha curcas* seed yields approach 6-8 MT/ha with ca 37% oil. Such yield could produce the equivalent of 2100-2800 liters of fuel oil/ha, whose energy is equivalent to 19,800-26,400 kwh/ha (Gaydou et al., 1982). Because of its very high saponification value and its ability to burn without emitting smoke, the oil of the seeds is commercially useful. For example, it is extensively used for making soap. The current economic, environmental and energy security concerns worldwide forces to shift from fossil fuels to biofuel alternatives such as bioethanol and biodiesel. Since biofuels can be produced from a diverse set of crops, each country is adopting a strategy that exploits the comparative advantages it holds in certain crops.

Among the different biofuel crops, *Jatropha curcas* is considered to be a better candidate for the production of biofuel because of the physiological and natural factors. The intense interest in oil from *Jatropha curcas* has generated enormous pressure to supply enough seeds that are homogenous and productive enough for plantation. Therefore, there is an urgent need to mass propagate elite trees. Equally urgent are methods to improve various agronomical traits of *Jatropha curcas*. Genetic engineering is recognized as a fast method for crop improvement. Plant transformation is essentially a two step process, i.e., delivery of genes into a host cell followed by regeneration of the transformed cell into a plant. Somatic embryogenic calli or somatic embryogenic suspension cultures is generally regarded as the most efficient method of regeneration as most of the transformed cells have already acquired the embryogenic potential that will drive them to develop into a somatic embryo quite spontaneously, a process similar to a fertilized egg cell in a zygotic embryo (Dodeman, et al., 1997).

Somatic embryos are suitable for transformation via *Agrobacterium tuniefaciens* (Mathews et al., 1992), microinjection (Neuhaus et al., 1987) and particle bombardment (Wilde et al., 1992). In addition, somatic embryos or somatic embryogenic calli can be cryopreserved using liquid nitrogen without loss of viability. This they are ideal materials for maintenance of germplasm as well as cell embryogenecity.

Somatic embryos are clonal in origin and thus multiplication using somatic embryos can have the potential for exceedingly high rates of vegetative increase and is therefore of considerable commercial interest. Regeneration via somatic embryogenesis is an attractive option for plant tissue culture. Somatic embryos reportedly provide more stable regenerants than shoots. Another advantage of regeneration systems using somatic embryos is their apparent single cell origin. This means that it is unlikely that regenerants are of chimerical origin, since, if a regenerant originates from a cluster of cells rather than a single sell, the plant tissues may be chimerical or unstable and produce off-types.

To further improve this crop, biotechnological techniques such as tissue culture and transformation can be utilized. Over two decades several reports were documented on *Jatropha* regeneration using various explants using different composition of media. These reports include plant regeneration from hypocotyl, petiole, and leaf explants (Sujatha and Mukta, 1996), epicotyl explants (Chinese Patent Application No. 200610020449.X), leaf disc (Indian Patent Application Publication No. 490/MUM/2006), shoot tip and nodal explants (European Patent Application Publication No. 1817956; Datta et al., 2007), somatic embryogenesis from leaf callus (Jha et al., 2007), and transformation from cotyledon disc explants (Li et al., 2008). All of the above studies focused on callus-mediated and meristematic tissue regeneration. Production of plantlets via organogenesis or somatic embryogenesis from reproductive tissues (anthers or ovules) may lead to the production of haploids, double haploids or diploids which may result in true to type homozygous character, paying the way from plant breeding program.

Ploidy determinations have traditionally been done by counting chromosomes of stained root tips, but this method is laborious and often difficult with species which have small chromosomes and high ploidy levels and can lead to misclassified germplasm (Brummer et al., 1999). All chromosomes are located in the cell nucleus of plants enabling nuclear DNA content to be used as an estimate of ploidy level. In recent years; flow cytometry has become the preferred technique for estimating the nuclear DNA content because of its ease, quickness, and accuracy (Rayburn et al., 1989; Heslop-Harrison, 1995). Arumuganathan and Earle (1991a) determined nuclear DNA contents of more than 100 major crop plant species using flow cytometry. Vogel et al. (1999) used flow cytometry to determine the base DNA content of the genomes in the perennial Triticeae. Flow cytometry also has been used to determine the ploidy level of switchgrass (*Panicum virgatum* L.) (Hultquist et al., 1997; Lu et al., 1998), alfalfa (*Medicago sativa* L.) (Brummer et al., 1999) and turfgrass species (Arumuganathan et al., 1999). The amount of DNA in plant cells is expressed in picograms (pg) as a "C" value (Bennett and Smith, 1976). The letter C stands for a "constant" or the amount of DNA in a haploid nucleus or genome; 2C values represent the DNA content of a diploid somatic nucleus. DNA amounts in picograms can be converted to megabase pairs (Mbp) by means of the conversion factor of 1 pg=980 Mbp (Bennett et al., 2000).

Therefore, there remains a need in the art for regeneration of plantlets via somatic embryogenesis using reproductive tissues (anthers or ovules). Despite these reported success, in this investigation we report for the first time, high frequency regeneration via somatic embryogenesis from ovule explants isolated from unopened flower buds of *Jatropha curcas* which are economical and allow production of haploids, double haploids or diploids and disease-free plantlets.

SUMMARY OF THE INVENTION

The present invention relates to the field of somatic embryo production, particularly to methods for somatic embryogenesis of *Jatropha* from ovules. More specifically, the present invention relates to a method and media compositions for somatic embryogenesis of *Jatropha curcas* from ovules of unopened flower buds. The method is well suited for *Jatropha curcas* transformation, for producing clonal planting stock useful for large scale *Jatropha curcas* plantation and for producing haploids, double haploids, diploids and disease-free plantlets. The method also enables high efficiency transformation of this plant.

Thus, in one aspect the present invention provides a method for producing somatic embryos from explants obtained from ovules of *Jatropha curcas*. In accordance with this aspect, explants are obtained from healthy mother *Jatropha curcas* plants. In one embodiment, the ovule explant is obtained from an unopened flower bud. In another embodiment, the ovule is unfertilized. In a further embodiment, the ovule explant is sterilized. The ovule explants are placed on a solid culture initiation medium comprising MS basal medium (Murashige and Skoog, 1962) and containing an auxin for callus induction and somatic embryogenesis. In one embodiment, the auxin is 2,4-dichlorophenoxyacetic acid (2,4-D). In one embodiment, the ovule explants are cultured on the initiation medium in the dark for the formation of embryogenic callus. In another embodiment, the embryogenic callus is transferred to fresh initiation medium and cultured in the light for somatic embryo development and maturation. The mature somatic embryos are transferred to a solid germination medium having basal salts of MS medium and containing auxin and gibberellic acid ($GA_3$). In one embodiment, the auxin is indole-3-butyric acid (IBA). In one embodiment, the germination medium also contains one or more cytokinins. In another embodiment, the germination medium also contains one or more organic additives. In a further embodiment, the germination medium also contains one or more cytokinins and one or more organic additives. In one embodiment, the cytokinin is kinetin (KN), 6-benzylaminopurine (BA), cytokinin-active urea derivatives (such as thidiazuron (TDZ)) or mixtures thereof. In one embodiment, the organic additive is casein hydrolysate (CH), adenine sulphate ($AdSO_4$) or mixtures thereof. In one embodiment, the mature somatic embryos are cultured on the germination medium in the light. The germinated plantlets are hardened and transferred to a greenhouse.

The method of the present invention comprises a complete and efficient system which can be used for regeneration of plants in the genera of *Jatropha*, more specifically in the *Jatropha curcas* species and its artificial hybrids. Numerous somatic embryos have been produced by this system and the regenerants have been demonstrated to be completely normal in vegetative development and sexual preproduction.

As shown herein, the plantlets produced from unfertilized ovules through the somatic embryogenesis method are haploid. Diploid plants, for example, double haploid plants, are produced by treating embryogenic callus with a mitotic inhibitor, such as colchicine or oryzalin.

BRIEF DESCRIPTION OF THE FIGURES

FIG. 1A: Callus initiation from ovules after 20 days. FIG. 1B: Embryogenic callus initiation from ovules after 40 days. FIG. 1C: Origination of somatic embryos from ovular callus. FIG. 1D: Development of different stages of somatic embryos (globular, heart shaped, torpedo and cotyledonary stage) from ovular callus after 75 days. FIG. 1E and FIG. 1F: Development of secondary somatic embryos from primary somatic embryos after 90 days (tor: torpedo-shaped somatic embryos; glo: globular somatic embryos).

FIG. 2A: Embryogenic callus initiation from ovules. FIG. 2B: Globular stage embryo (glo) and heart shaped embryo (h). FIG. 2C: Torpedo shaped embryo (tor). FIG. 2D and FIG. 2E: Cotyledon shaped somatic embryos (cot) (early and late stage). FIG. 2F: Germinated somatic embryos (r: root).

FIG. 3A: Plant produced herein. FIG. 3B: DNA content of control diploid plant determined by flow cytometry shows 2c. FIG. 3C: DNA content of plant of FIG. 3A by determined by flow cytometry shows 1c indicating that the plant is haploid.

DETAILED DESCRIPTION OF THE INVENTION

Figure 1:
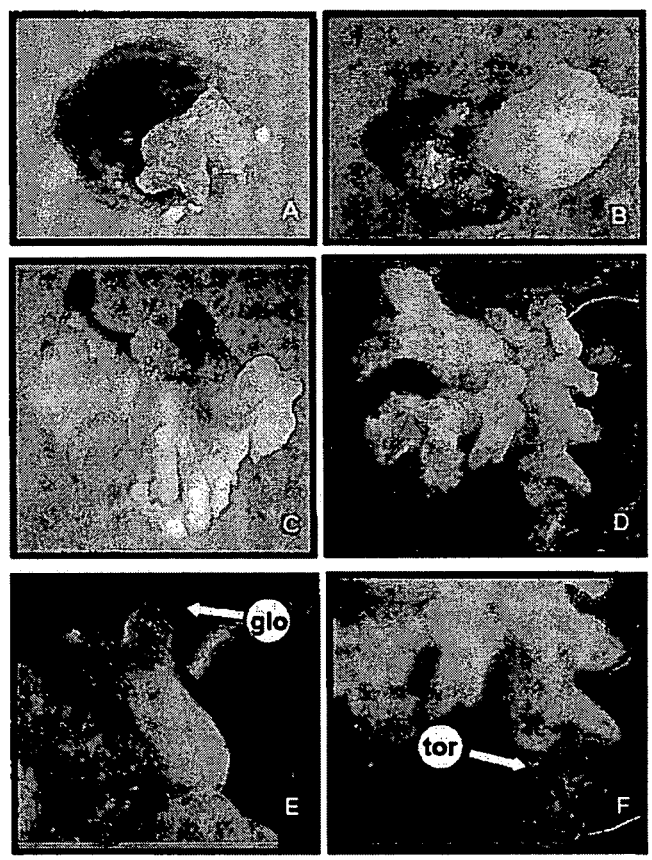
FIGS. 1A-1F show somatic embryogenesis from ovules of *Jatropha curcas* L.

The present invention relates to the field of somatic embryo production, particularly to methods for somatic embyrogenesis of *Jatropha* from ovules. More specifically, the present invention relates to a method and media compositions for somatic embryogenesis of *Jatropha curcas* from ovules of unopened flower buds. The method is well suited for *Jatropha curcas* transformation, for producing clonal planting stock useful for large scale *Jatropha curcas* plantation and for producing haploids, double haploids, diploids and disease-free plantlets. The method also enables high efficiency transformation of this plant.

Propagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Vegetative propagation via somatic embryogenesis has the capability to capture all genetic gain of highly desirable genotypes. Furthermore, these methods are readily amenable to automation and mechanization. Finally, high efficiency transformation of plants can be accomplished using somatic embryogenesis to regenerated transformed cells.

In accordance with the present invention, somatic embryos are produced by inducing somatic embryo formation on explant tissue. In one embodiment, somatic embryos are induced from explants obtained from ovules of a plant of the genera *Jatropha*. In one embodiment, the ovules are obtained from unopened flowers. In another embodiment, the ovules are unfertilized. The ovule explants are placed on a solid medium referred to herein as initiation medium. In one embodiment, the initiation medium is MS medium and contains an auxin. In one embodiment, the auxin is 2,4-D. In one embodiment, the concentration of 2,4-D in the initiation medium is about 2.26 µM to about 9.04 µM, preferably about 4.52 µM to about 6.78 µM, more preferably about 6.78 µM. In one embodiment, the initiation medium also contains a source of carbon. In one embodiment, the source of carbon is sucrose at about 2% to about 5%, preferably about 2% to about 3%, more preferably about 3%. In another embodiment, the source of carbon is glucose at about 2% to about 5%, preferably about 3% to about 5%. In an additional embodiment, the source of carbon is fructose at about 2% to about 5%, preferably about 2% to about 3%. In a further embodiment, the source of carbon is maltose at about 2% to about 5%, preferably about 2% to about 3%. In another embodiment, the source of carbon is a mixture of sucrose and glucose at about 2% to about 3%, preferably about 2% sucrose and about 2% to about 3%, preferably about 2% glucose. In an additional embodiment, the source of carbon is a mixture of fructose and glucose at about 1% to about 2%, preferably about 1% fructose and about 2% to about 3%, preferably about 2% glucose. In a further embodiment, the source of carbon is a mixture of maltose and glucose at about 1% to about 2%, preferably about 1% maltose and about 2% to about 3%, preferably about 2% glucose.

In one embodiment, the ovule explants are cultured on the initiation medium for about 30 days to about 60 days, preferably about 40 days. In one embodiment, the culture is maintained at about 25° C.±2° C. in the dark at 55% to 60% relative humidity. Culturing the ovule explants on the initiation medium induces the formation of embryogenic callus.

After culturing on the initiation medium in the dark to induce embryogenic callus formation, the embryogenic callus tissue is placed on fresh initiation medium for the development and maturation of somatic embryos. In one embodiment, the embryogenic callus tissue is cultured on initiation medium for about four weeks to about six weeks, preferably four weeks. In one embodiment, the embryogenic callus tissue with developing and maturing somatic embryos is subcultured at two week intervals. In one embodiment, the culture of embryogenic callus tissue to develop and mature somatic embryos is maintained at about 25° C.±2° C. with a 16 h/8 h (light/dark) photoperiod at 55% to 60% relative humidity. In one embodiment, the light photoperiod is under white fluorescent lights with a light intensity of about 25 µE $m^{-2}s^{-1}$.

After culturing to produce mature somatic embryos, the somatic embryos are placed on a solid medium referred to herein as germination medium. In one embodiment the mature somatic embryos are cotyledon-shaped somatic embryos. In one embodiment, the germination medium is MS medium and contains an auxin and $GA_3$. In one embodiment, the auxin is IBA. In one embodiment, the concentration of IBA in the germination medium is about 1.23 µM to about 4.92 µM, preferably about 1.84 µM to about 2:46 more preferably about 2.46 µM. In one embodiment, the concentration of $GA_3$ in the germination medium is about 0.72 µM to about 5.76 µM, preferably about 1.44 µM to about 2.88 µM, more preferably about 2.88 µM. In one embodiment, the germination medium further contains one or more cytokinins. In one embodiment, the cytokinin is KN, BA, cytokinin-active urea derivatives (such as TDZ) or mixtures thereof. In one embodiment, the concentration of KN is about 1.16 µM to about 9.28 µM, preferably about 2.32 µM to about 4.64 µM, more preferably about 4.64 µM. In another embodiment, the concentration of BA is about 1.10 µM to about 8.86 µM, preferably about 2.21 µM to about 4.43 µM, more preferably about 4.43 µM. In a further embodiment, the concentration of TDZ is about 1.13 µM to about 9.08 µM, preferably about 2.27 µM to about 4.54 µM, more preferably about 4.54 µM. In an additional embodiment, the cytokinin is a mixture of KN and BA in amounts of about 1.16 µM to about 4.64 µM, preferably 1.16 µM to about 2.32 µM, more preferably about 2.32 µM KN and about 1.10 µM to about 4.43 µM, preferably 1.10 µM to about 2.21 µM, more preferably about 2.21 µM BA. In another embodiment, the cytokinin is a mixture of BA and TDZ in amounts of about 1.10 µM to about 4.43 µM, preferably 1.10 µM to about 2.21 µM, more preferably about 2.21 µM BA and about 1.13 µM to about 4.54 µM, preferably 1.13 µM to about 2.27 µM, more preferably about 2.27 µM TDZ. In a further embodiment, the cytokinin is a mixture of KN and TDZ in amounts of about 1.16 µM to about 4.64 µM, preferably 1.16 µM to about 2.32 µM, more preferably about 2.32 µM KN and about 1.13 µM to about 4.54 µM, preferably 1.13 µM to about 2.27 µM, more preferably about 2.27 µM TDZ. In another embodiment, the germination medium further contains one or more organic additives. In one embodiment, the organic additive is CH, $AdSO_4$ or mixtures thereof. In one embodiment, the germination medium is supplemented with about 0.25 g to about 1.5 g, preferably about 0.5 g to about 1.0 g, more preferably about 1.0 g CH. In one embodiment, the germination medium is supplemented with about 25 mg to about 200 mg, preferably about 50 mg to about 100 mg, more preferably about 100 mg AdSO$_4$. In a further embodiment, the germination medium is supplemented with one or more cytokinins and one or more organic additives. The germination medium also contains a source of carbon. The source of carbon in the germination medium may be the same as in the initiation medium. In a preferred embodiment, the source of carbon is sucrose at about 2% to about 5%, preferably about 2% to about 3%, more preferably, about 3%.

In one embodiment, the mature somatic embryos are cultured on the germination medium for about one week to about three weeks, preferably two weeks. In one embodiment, the mature somatic embryos are subcultured at two week intervals. In one embodiment, the culture of mature somatic embryos is maintained at about 25° C.±2° C. with a 16 h/8 h (light/dark) photoperiod at 55% to 60% relative humidity. In one embodiment, the light photoperiod is under white fluorescent lights with a light intensity of about 25 µE m$^{-2}$s$^{-1}$. The germinated somatic embryos, i.e., plantlets are then hardened. In one embodiment, the plantlets are hardened on soil, sand, moss, charcoal (1:1:2:0.5 v/v/v/v) or other Houghland soil alone or in a combination of defined ratio of Houghland soil and sand (2:1 v/v).

The plantlet produced from unfertilized ovules by the somatic embyrogenesis method described herein produces a haploid plant as demonstrated by an analysis of DNA content by flow cytometry.

Double haploid plants are produced by treating the embryogenic callus with a mitotic inhibitor. In one embodiment, the embryogenic callus is treated with the mitotic inhibitor for one day to three days, preferably three days. In one embodiment, the mitotic inhibitor is colchicine. In one embodiment, the embryogenic callus is treated with 0.1% to 0.5%, preferably 0.5% colchicine. In another embodiment, the mitotic inhibitor is oryzalin. In one embodiment, the embryogenic callus is treated with 0.1% to 0.5%, preferably 0.5% oryzalin. The mitotic inhibitor is added to the embryogenic callus induction medium, described above, prior to transfer of the embryogenic callus to the fresh initiation medium. The culture conditions for culturing in the presence of the mitotic inhibitor is the same as for somatic embryogenic callus induction. Following treatment with the mitotic inhibitor, the treated embryogenic callus is placed on fresh initiation medium for the development and maturation of somatic embryos and cultured as described above. The mature somatic embryos are placed on the germination medium and cultured as described above to germinate double haploid plantlets as described above.

In addition, the present invention provides systems which can be used for the transformation of plants of the genera *Jatropha*. The method of transformation/transfection is not critical to the transformation of plants of the genera *Jatropha*; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed. See, for example, Mathews et al. (1992), Neuhaus et al. (1987), Wilde et al. (1992), U.S. Pat. Nos. 7,241,937, 7,273,966 and 7,291,765 and U.S. Patent Application Publication Nos. 2007/0231905 and 2008/0010704. See also, International Published Application No. WO2005/103271.

In one embodiment, the explant tissue can be co-cultured with an *Agrobacterium* strain harboring a DNA construct containing a gene or nucleic acid of interest using techniques well known in the art. Transformed tissue can be selected using conventional techniques well known in the art. In another embodiment, the embryogenic liquid suspension cultures can be co-cultured with an *Agrobacterium* strain harboring a DNA construct containing a gene or nucleic acid of interest using techniques well known in the art. Transformed tissue can be selected using conventional techniques well known in the art. In a further embodiment, the DNA can be introduced into the explant tissue or cells of the embryogenic liquid suspension culture using conventional techniques, such as particle bombardment. Transformed tissue can be selected using conventional techniques well known in the art. Transformed or transgenic plants can be regenerated using the methods described herein.

Similarly, the DNA that is inserted (the DNA of interest) into plants of the genera *Jatropha* is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence or a miRNA sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes. See, U.S. Pat. No. 7,205,453 and U.S. Patent Application Publication Nos. 2006/0218670 and 2006/0248616.

Generally, the expression cassette will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-diclalorophenoxyacetate (2,4-D), including genes coding for resistance to herbicides which act to inhibit the action of glutamine synthase such as phosphinothricin or basta (e.g., the bar gene). See generally, WO 02/36782, U.S. Pat. No. 7,205,453 and U.S. Patent Application Publication Nos. 2006/0248616 and 2007/0143880, and those references cited therein. This list of selectable marker genes is not meant to be limiting. Any selectable marker gene can be used.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV$^{35S}$ promoter (Odell et al., 1985); rice actin (McElroy et al., 1990); ubiquitin (Christensen and Quail, 1989; Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506, 962, 6,575,814, 6,972,349 and 7,301,069 and in U.S. Patent Application Publication Nos. 2007/0061917 and 2007/0143880.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley—VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Preparation of Mother Plant

In certain embodiments, the mother plant from which the explants are harvested is subject to screening to identify healthy specimens and/or treatment to either maintain a disease-free state or to treat existing disease. Health can be determined by assessing the plants for their size, weight, general growth, appearance, and absence of infection or contamination. *J. curcas* plants are commonly infected with "frogeye" (*Cercospera* spp.), insects of the order of *Heteroptera* and the golden flea beetle (*Podagrica* species). Decontamination can be performed by spraying the plants with agents such as fungicides, insecticides, pesticides or the like. Preferred fungicides for the pretreatment of the mother plant include Bavistin™, Captan™, Dithane or combinations thereof at a concentration of about 0.05% to 0.2%. Preferred insecticides for the pretreatment of the mother plant include, but are not limited to, Rogor™, Nuvacron, Fastac™, Ultracid™ 40-WP, Thiodane™ at a concentration of about 0.005% to 0.02%.

Example 2

Sterilization of Unopened Flower Buds

The unopened flower buds of *Jatropha curcas* L. were collected from the mother plants in green house of Temasek Lifesciences Laboratory, 1 Research Link, National University of Singapore, Singapore 117604 (Kindly provided by Dr. Hong Yon). The flower buds were washed in chlorohexidine surgical wash (two drops in 100 ml of sterile water) for twenty minutes and later these buds were further surface sterilized in 10% clorox solution (commercial bleach) for fifteen minutes followed by washes with sterile water for five times. To ensure complete sterility, these buds were rinsed again with 70% alcohol for three minutes and subsequently washed with sterile water three times before dissection to isolate ovule as explants.

Example 3

Media and Hormones

The initiation medium was MS basal medium (MS mineral salts and vitamins) supplemented with sucrose (3%) as the carbon source and included phytoagar (0.8%) as a gelling agent. The pH of the medium was 5.8. The germination medium was MS basal medium supplemented with sucrose (3%) as the carbon source and included phytogel (0.25%) as a gelling agent. The pH of the medium was 5.8. The media were dispensed into sterilized Petri dish (90×15 mm size, plastic polycarbonate, Canada). The chemicals used for media preparations were of analytical grade (Duchefa Biochemie, Haarlem, The Netherlands and Sigma Aldrich, Inc., St Louis, USA).

Different hormones were added to the media for the development of the method according to the present invention. In general, the media contained a reduced concentration of phytohormones. The hormones that were tested in the media were phytohormones that will affect growth in the desired manner during different stages of tissue culture. Examples of phytohormones that were tested include natural or synthetic auxin (2,4-D, indole-3-acetic acid (IAA), IBA, cytokinin (BA, KN,), $GA_3$, or cytokinin-active urea derivatives (such as TDZ). The hormones were tested singly or in combination. For induction of embryogenic callus, only 2,4-D (2.26, 4.52, 6.78 and 9.02 µM) was effective. Other auxins IAA (0.71, 1.42, 2.85, 5.70 µM), IBA (0.615, 1.23, 2.46, 4.92 µM) and combination of 2,4-D (2.26, 4.52, 6.78 and 9.02 µM) or IAA (0.71, 1.42, 2.85, 5.70 µM) or IBA (0.615, 1.23, 2.46, 4.92 µM) with cytokinins, BA (1.10, 2.20, 4.43 µM), KN (1.16, 2.32, 4.64 µM) and TDZ (1.13, 2.27, 4.54 µM) individually and in combinations induced only non-embryogenic callus.

For germination of somatic embryos, the combination of IBA (1.23, 1.84, 2.46, 4.92 µM) and $GA_3$ (0.72, 1.44, 2.88, 5.76 µM) was effective. IAA (1.42, 2.85, 5.7, 8.56 µM) and NAA (1.34, 2.68, 5.37, 8.04 µM) in combination with $GA_3$ (0.72, 1.44, 2.88, 5.76 µM) were tried but not effective. Addition of cytokinins (1.16, 2.32, 4.64, 9.28, µM KN; 1.10, 2.21, 4.43, 8.86 µM BA; 1.13, 2.27, 4.54, 9.08 µM TDZ; 1.16, 2.32, 4.64 µM KN and 1.10, 2.21, 4.43 µM BA; 1.10, 2.21, 4.43 µM BA and 1.13, 2.27, 4.54 µM TDZ; 1.16, 2.32, 4.64 µM KN and 1.13, 2.27, 4.54 µM TDZ) and/or organic additives (0.25 g, 0.5 g, 1.0 g CH; 25 mg, 50 mg, 100 mg, 200 mg $AdSO_4$; or combinations thereof) enhanced the growth of germinated plantlets.

Example 4

Isolation and Culture of Ovule Explants

The sterilized flower buds were dissected using stereo microscope and the ovules were isolated and injured using dissection needle. The injured ovule explants were inoculated onto initiation medium supplemented with different phytohormones and incubated in dark for 40 days. The callus induced from these ovules was transferred to the fresh initiation medium and cultured in the light (16/8 h (light/dark) photoperiod period, light intensity of 25 µE $m^{-2}s^{-1}$) for somatic embryo development and maturation. The callus with developing and maturing somatic embryos were subcultured every two weeks. The mature cotyledon shaped somatic embryos that developed from this embryogenic callus were transferred to germination medium for germination. The germinating somatic embryos were subcultured every two weeks. The germinated plantlets were hardened and transferred to green house. All cultures were maintained at 25° C.±2° C. with 55%-60% relative humidity. Approximately 12-15 mature cotyledon shaped embryos were developed per 100 mg of embryogenic callus, and 95% of the somatic embryos were developed.

Example 5

Somatic Embryogenesis of *Jatropha curcas*

*Jatropha curcas* is considered to be a better candidate for the production of biofuel because of its high oil content and has lately attracted particular attention as a tropical energy plant. Because of these physiological factors of possessing high oil content, it is important to improve its biomass production. For this reason, biotechnological techniques such as tissue culture and transformation can be utilized. Although there are reports on callus and meristematic tissue regeneration (Sujatha and Mukta, 1996; Chinese Patent Application No. 200610020449; Indian Patent Application Publication No. 490/MUM/2006; (European Patent Application Publication No. 1817956; Datta et al. 2007) and somatic embryogenesis from leaf callus (Jha et al. 2007), there has been no report of regeneration through somatic embryogenesis using reproductive organs specially unfertilized ovule as explants in *J. curcas*. In the present study we have standardized regeneration through somatic embryo genesis using unfertilized ovules of *J. curcas*.

Figure 2:
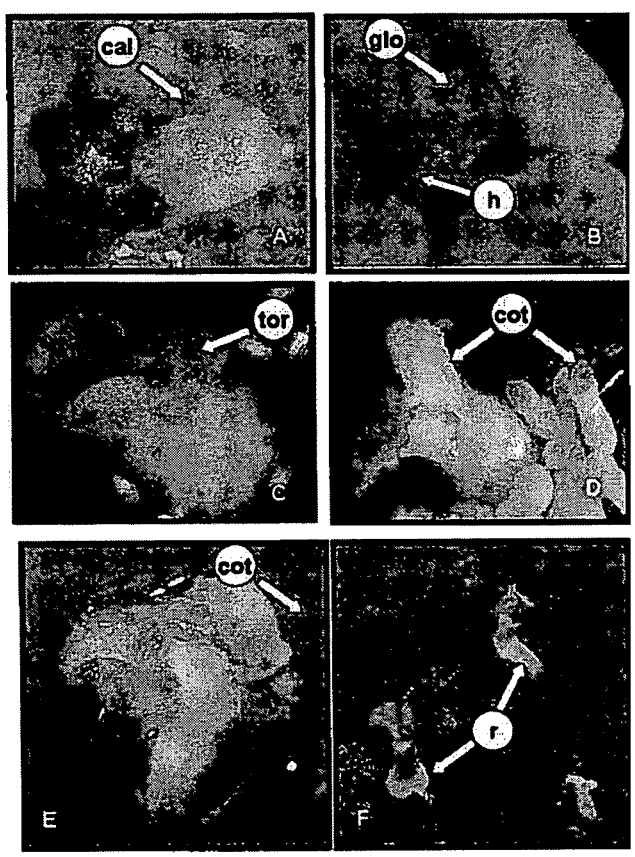
FIGS. 2A-2F show different stages of somatic embryos from ovules of *Jatropha curcus* L.

Induction of callus occurred in MS medium containing different auxins and cytokinins individually as well as in combinations. Among the different media type, MS medium containing 2,4-D were effective in inducing embryogenic callus (FIGS. 1A, 1B and FIG. 2A shown using 6.78 µM 2,4-D) and somatic embryo development (globular, heart, torpedo and cotyledon-shaped) (FIGS. 1C and 1D, FIGS. 2A-2E). The use of other phytohormones did not result in the induction of embryogenic callus. Continuous culture of somatic embryos in MS medium containing 2,4-D resulted in abnormal somatic embryo formation without germination.

It is to be noted that, light played a major role in the induction of embryogenic callus. Culture of ovules in MS medium supplemented with 2,4-D under dark conditions induced embryogenic callus. However, culture of ovules in MS medium supplemented with 2,4-D under in the presence of light idd not result in the induction of embryogenic callus. Similarly, somatic embryos developed only in light conditions and not in dark conditions.

The germination of somatic embryos occurred in MS medium supplemented with $GA_3$ and IBA. Addition of cytokinins (KN, BA, TDZ, KN/BA, KN/TDZ and BA/TDZ) and organic additives (CH, $AdSO_4$ and CH/$AdSO_4$) enhanced growth of germinated plantlets. It was also observed that along with primary somatic embryos, secondary somatic embryos also occurred (FIGS. 1E and 1F).

In contrast, Jha et al. (2007) have reported that, embryogenic callus from leaf explants of *J. curcas* were induced on MS medium supplemented with KN (9.3 µM) and somatic embryos were developed on MS medium supplemented with KN (2.3 µM) and IBA (1.0 µM). Jha et al. (2007) also reported that, addition of adenine sulphate (13.6 µM) stimulated the process of somatic embryo development. In the present study, the addition of $AdSO_4$ in callus induction medium resulted in induction of greenish compact callus that becomes non-embryogenic. Only 2,4-D and dark conditions was vital for induction of embryogenic callus induction. Similar results were reported by Kim et al. (2007) in *Podophyllum peltatum*. Jha et al. (2007) have stated that somatic embryogenic system in *J. curcas* takes twelve-sixteen weeks whereas in the present study, the entire somatic embryogenic system can be completed in less than twelve-weeks with 95% somatic embryo germination. As somatic embryos are developed from unfertilized ovules, this system can be used for production of haploids, double haploids or diploid plants which are useful in plant breeding and in creating transgenic plants.

Example 6

Determination of Ploidy of Regenerated Plants

The objective of this study were to determine the nuclear DNA content of somatic embryo derived plantlets from unfertilized flower buds of *Jatropha curcas* L and in vivo grown diploid plants whose chromosome number is 2n=22.

The procedures described by Arumuganathan and Earle (1991b) and Tuna et al. (2001) were used to determine DNA content per nucleus. Briefly, the procedure consists of preparing suspensions of intact nuclei by chopping plant tissues and lysing protoplasts in a $MgSO_4$ buffer mixed with DNA standards and staining the nuclei with propidium iodide (PI) in a solution containing DNase-free RNase. Fluorescence intensifies of the stained nuclei were estimated by comparing fluorescence intensities of the nuclei of the diploid in vivo *Jatropha curcas* plants.

Approximately 500 mg of fresh, green tissue from young somatic embryo derived shoots was excised and placed on ice in a sterile 35-by 10 mm plastic Petri dish. About 500 mg of leaf tissues from *Jatropha* seedlings were added as a standard. The leaf tissue was chopped into 0.25-1.0 mm segments in 1 ml of solution A (24 ml $MgSO_4$ buffer (ice-cold); 25 mg dithiothreitol; 500 µl propidium iodide stock (5.0 mg propidium iodide in 1.0 ml double distilled water); 625 µl Triton X-100 stock (1.0 g Triton X-100 in 10 ml ddH2O). The homogenate was filtered through a 33-µm nylon mesh into a microcentrifuge tube and centrifuged (VS-15 microcentrifuge, Shelton Scientific, Shelton, Conn.) at 13000 RPM for 20 s. The supernatant was discarded, the pellet was resuspended in 4000 of solution B (7.5 ml solution A; 173 µl RNase (DNase free) and it was incubated for 15 minutes at 37° C. before flow cytometric analysis.

The prepared material was analyzed in a nano drop spectrophotometer. For measurement, PI fluorescence area signals (FL2-A) from 20,000 nuclei were collected by CellQuest software (Becton Dickinson Immuno cytometry system, San Jose, Calif.). A live gate instrument configuration was used by employing the FL2-A and FSC-H parameters which allowed the fluorescence measurement from nuclei to be used to generate a histogram of FL2-A. Mean position of G0/G1 (nuclei) peak of sample and internal standard were determined by analyzing the data by CellQuest software. The mean DNA content per plant was based on the 20000 scanned nuclei. The formula used for converting florescence values to DNA content was: Nuclear DNA content=(mean position of unknown peak)/(mean position of known)×DNA content of known standard.

Figure 3:
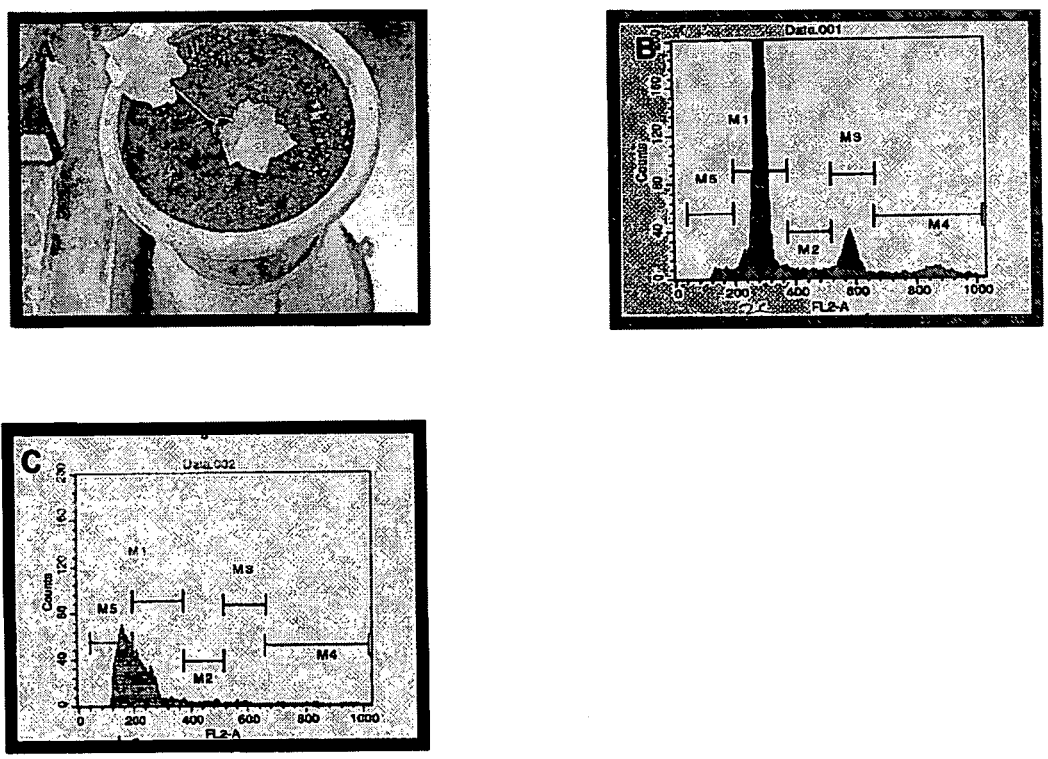
FIGS. 3A-3C show the analysis of ploidy in a plant regenerated in accordance with the present invention.

The flow cytometric analysis of young leaves of diploid control plants of *Jatropha curcas* showed two peaks of DNA pulse amplitude signal corresponding to 2C and 4C chromosomal content (FIG. 3B). In case of somatic embryo derived plantlets (FIG. 3A), only one peak was seen that was lesser than DNA pulse amplitude signal corresponding to 2C chromosomal content and approximately half of 2C DNA content (FIG. 3C). This single peak observation indicated that the plants to be haploid with chromosome number n=11 and the two peaks observed from the control plants shows the plant to be diploid with chromosome number 2n=22. The DNA content of leaves of haploid and diploid plants were quantified and it was observed that the leaves of haploid and diploid plants contains 254.15 ng/µl and 508.3 ng/µl respectively. As the plantlets were regenerated via callus mediated somatic embryogenesis from the ovules isolated from the ovary of unfertilized flower buds of *J. curcas*, the plantlets are haploid, confirmed by flow cytometry. Similar observation of haploid production from in vitro culture of unpollinated ovules of *Cucurbita pepo* and sugar beet (*Beta vulgaris* L.) were reported (Metwally et al. (2004); Gürel and Gürel (1998); Bossoutrot and Hosemans. (1985); Galatowitsch and Smith (1990); Van Geyt et al. (1987)). The production of haploid plants from unfertilized plants is the first report in *Jatropha curcas*.

Example 7

Production of Double Haploid Regenerated plants of *Jatropha curcas*

Embryogenic callus prepared as described in Example 5 which is above to develop into somatic embryos (after forty days of embryogenic callus induction) was treated with different concentration of colchicines (0.1-1%) for three-days. The culture condition (temperature, photoperiod and light) are same as described above. After the colchicine treatment, the treated embryogenic callus was transferred to fresh initiation medium (MS medium containing 2,4-D (6.78 µM)) and cultured as described in Example 5 for the development of somatic embryos. The mature somatic embryos were transferred to germination media (MS medium fortified with $GA_3$ and IBA) and cultured as described in Example 5 for plantlet development.

Among the different colchicines treatment, 0.5% concentration was most effective in production of double haploid plantlets. If the concentration increased above 0.5% the callus become brown and died. The morphological characters of colchicines treated plantlets are like double haploid. This technique can be further applied for plant breeding programs.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Arumuganathan, K. and Earle, E. D. (1991a). Nuclear DNA content of some important plant species. *Plant Mol Biol Rep* 9:208-219, (1991a).

Arumuganathan, K. and Earle, E. D. (1991b). Estimation of nuclear DNA content of plants by flow cytometry. *Plant Mol Biol Rep* 9:221-231.

Arumuganathan, K. et al. (1999). Nuclear DNA content of thirteen turfgrass species by flow cytometry. *Crop Sci* 39:1202-1207.

Bennett, M. D. et al. (2000). Nuclear DNA amounts in angiosperms and their modern uses-807 new estimates. *Ann Bot* (London) 86:859-909.

Bossoutrot, D. and Hosemans, D. (1985). Gynogenesis in *Beta vulgaris* L. from in vitro culture of unpollinated ovules to production of doubled haploid plants in soil. *Plant Cell Rep* 4:300-303.

Brummer, E. C. et al. (1999). Ploidy determination of alfalfa germplasm accession using flow cytometry. *Crop Sci* 39:1202-1207.

Christensen, A. H. and Quail, P. H, (1989). Sequence analysis and transcriptional regulation by heat shock of polyubiquitin transcripts from maize. *Plant Mol Biol* 12:619-632.

Christensen, A. H. et al. (1992). Maize polyubiquitin genes: structure, thermal perturbation of expression and transcript splicing, and promoter activity following transfer to protoplasts by electroporation. *Plant Mol Biol* 18:675-689.

Datta, M. M. et al. (2007). In vitro clonal propagation of biodiesel plant (*Jatropha curcas* L.). *Curr Sci* 93:1438-1442.

Dodeman, V. L. et al. (1997). Zygotic embryogenesis versus somatic embryogenesis. *J Exp Bot* 48:1493-1509.

Galatowitsch, M. W. and Smith G. A. (1990). Regeneration from unfertilized ovule callus of sugar beet (*Beta vulgaris* L.). *Can. J. Plant Sci* 70:83-89.

Gaydou, A. M. et al. (1982). Vegetable energy sources in Madagascar: ethyl alcohol and oil seeds (French). *Oleagineux* 37:135-141.

Gürel, E. and Gürel, S. (1998). Plant regeneration from unfertilized ovaries of sugar beet (*Beta vulgaris* L.) cultured in vitro. *Tr J Botany* 22:233-238.

Heslop-Harrison, J. S. (1995). Flow cytometry and genome analysis. *Probe* 5:14-17.

Hultquist, S. J. et al. (1997). DNA content and chloroplast DNA polymorphisims among accessions of switchgrass from remnant Midwestern prairies. *Crop Sci* 37:595-98.

Jha, T. B. et al. (2007). Somatic embryogenesis in *Jatropha curcas* Linn., an important biofuel plant. *Plant Biotech Rep* 1:135-140.

Kim, Y. S. et al. (2007). High frequency plant regeneration via somatic embryogenesis in *Podophyllum peltatum* L., an important source of anticancer drug. *Curr Sci* 92:662-666.

Last, D. I. et al. (1991). pEmu: an improved promoter for gene expression in cereal cells. *Theor Appl Genet* 81:581-588.

Li, M. et al. (2008). Establishment of an mediated cotyledon disc transformation method for *Jatropha curcas*. *Plant Cell Tiss and Org Cult* 92:173-181.

Lu, K. et al. (1998). Nuclear DNA content and chromosome numbers in switch grass. *Great Plains Res* 8:269-80.

Mathews, H. et al. (1992). Stable integration and expression of beta-glucuronidase and NPT-II genes in mango somatic embryos. *In Vitro Cell Develop Biol—Plant* 28P:172-178.

McElroy, D. et al. (1990). Isolation of an efficient actin promoter for use in rice transformation. Plant Cell 2:163-171.

Metwally, E. I. et al. (1998). Production of haploid plants from in vitro culture of unpollinated ovules of *cucubita pepo*. *Plant Cell Tiss Org Cult* 52:117-121.

Murashige, T. and Skoog, F. (1962). A revised medium for rapid growth and bioassays with tobacco tissue cultures. *Physiol Plant* 15:473-497.

Neuhaus, G. et al. (1987). Transgenic rapeseed plants obtained by microinjected DNA into microspore-derived embryoids. *Theor Appl Genet* 75:30-36.

Odell, J. T. et al. (1985). Identification of DNA sequences required for activity of the cauliflower mosaic virus 35S promoter. *Nature* 313:810-812.

Rayburn, A. L. et al. (1989). Detection of intraspecific DNA content variation in *Zea mays* L., by flow cytometry. *J Exp Bot* 40:1179-1183.

Sujatha, M and Mukta, N. (1996). Morphogenesis and Plant regeneration from tissue cultures of *Jatropha curcas*. *Plant Cell Tiss and Org Cult* 44:135-141.

Van Geyt, J. P. C. et al. (1987). In vitro induction of haploid plants from unpollinated ovules and ovaries of the sugar beet (*Beta vulgaris* L.). *Theor Appl Genet* 73:920-925.

Velten, J. et al. (1984). Isolation of a dual plant promoter fragment from the Ti plasmid of *Agrobacterium tumefaciens*. *EMBO J* 3:2723-2730.

Vogel, K. P. et al. (1999). Nuclear DNA content and radiosensitivity in Brassica and allied genera. *Jap J Breed* 19:350-356.

Wilde, H. D. et al. (1992). Expression of foreign genes in transgenic yellow-poplar plants. *Physiol* 98:114-120.

What is claimed is:

1. A method of regenerating *Jatropha* via somatic embryogenesis comprising the steps:
    (a) culturing a *Jatropha* explant on a first medium comprising MS basal medium and 2,4-dichlorophenoxy acetic acid (2,4-D) in the dark to induce embryogenic callus formation, wherein the *Jatropha* explant is a dissected ovule from an unopened flower bud;
    (b) culturing the embryogenic callus on the first medium in a light/dark photoperiod to induce somatic embryo development and maturation; and
    (c) culturing mature somatic embryos on a second medium comprising MS basal medium, indole-3-butyric acid (IBA) and gibberellic acid ($GA_3$) in a light/dark photoperiod to germinate plantlets.

2. The method of claim 1, wherein the length of culturing is:
    about 30 days to about 60 days on the first medium to induce embryogenic callus formation;
    about four weeks to about six weeks on the first medium to develop and mature somatic embryos; and
    about one week to about three weeks on the second medium to germinate plantlets.

3. The method of claim 2, wherein the length of culturing on each medium is:

about 40 days on the first medium to induce embryogenic callus formation;

about four weeks on the first medium to develop and mature somatic embryos; and about two weeks on the second medium to germinate plantlets.

4. The method of claim 1, wherein the length of culturing is:

about 30 days to about 60 days on the first medium to induce embryogenic callus formation;

about four weeks to about six weeks on the first medium with subculturing about every two weeks to develop and mature somatic embryos; and about one week to about three weeks on the second medium with subculturing about every two weeks to germinate plantlets.

5. The method of claim 4, wherein the length of culturing on each medium is:

about 40 days on the first medium to induce embryogenic callus formation;

about four weeks on the first medium to develop and mature somatic embryos; and about two weeks on the second medium to germinate plantlets.

6. The method of claim 1, wherein the second medium further contains one or more cytokinins, one or more organic additives or a mixture or one or more cytokinins and one or more organic additives.

7. The method of claim 6, wherein the cytokinin is kinetin (KN), 6-benzylaminopurine (BA), thidiazuron (TDZ) or mixtures thereof.

8. The method of claim 6, wherein the organic additive is casein hydrolysate (CH), adenine sulphate ($AdSO_4$) or mixtures thereof.

9. The method of claim 6, wherein (a) the cytokinin is kinetin (KN), 6-benzylaminopurine (BA), thidiazuron (TDZ) or mixtures thereof and (b) the organic additive is casein hydrolysate (CH), adenine sulphate ($AdSO_4$) or mixtures thereof.

10. The method of claim 1, wherein the media comprise:

first medium: MS basal medium and about 2.26 µM to about 9.04 µM 2,4-D; and second medium: MS basal medium, about 1.23 µM to about 4.92 µM IBA and about 0.72 µM to about 5.76 µM $GA_3$.

11. The method of claim 10, wherein the media comprise:

first medium: MS basal medium and about 6.78 µM 2,4-D; and second medium: MS basal medium, about 2.46 µM IBA and about 2.88 µM $GA_3$.

12. The method of claim 7, wherein the concentration of the one or more cytokinins is:

(a) about 1.16 µM to about 9.28 µM KN;
(b) about 1.10 µM to about 8.86 µM BA;
(c) about 1.13 µM to about 9.08 µM TDZ;
(d) about 1.16 µM to about 4.64 µM KN and about, 1.10 µM to about 4.43 µM BA;
(e) about 1.10 µM to about 4.43 µM BA and about 1.13 µM to about 4.54 µM TDZ; or
(f) about 1.16 µM to about 4.64 µM KN and about 1.13 µM to about 4.54 µM TDZ.

13. The method of claim 12, wherein the concentration of the one or more cytokinins is:

(a) about 4.64 µM KN;
(b) about 4.43 µM BA;
(c) about 4.54 µM TDZ;
(d) about 2.32 µM KN and about 2.21 µM BA;
(e) about 2.21 µM BA and about 2.27 µM TDZ; or
(f) about 2.32 µM KN and about 2.27 µM TDZ.

14. The method of claim 8, wherein the amount of organic additive is:

(a) about 0.25 g to about 1.0 g CH;
(b) about 25 mg to about 200 mg $AdSO_4$; or
(c) about 0.25 g to about 1.0 g CH and about 25 mg to about 200 mg $AdSO_4$.

15. The method of claim 14, wherein the amount of organic additive is:

(a) about 1.0 g CH;
(b) about 100 mg $AdSO_4$; or
(c) about 1.0 g CH and about 100 mg $AdSO_4$.

16. The method of claim 9, wherein (a) the concentration of the one or more cytokinins is:
 (i) about 1.16 µM to about 9.28 µM KN;
 (ii) about 1.10 µM to about 8.86 µM BA;
 (iii) about 1.13 µM to about 9.08 µM TDZ;
 (iv) about 1.16 µM to about 4.64 µM KN and about 1.10 µM to about 4.43 µM BA;
 (v) about 1.10 µM to about 4.43 µM BA and about 1.13 µM to about 4.54 µM TDZ; or
 (vi) about 1.16 µM to about 4.64 µM KN and about 1.13 µM to about 4.54 µM TDZ; and (b) the amount of organic additive is:
 (i) about 0.25 g to about 1.0 g CH;
 (ii) about 25 mg to about 200 mg $AdSO_4$; or
 (iii) about 0.25 g to about 1.0 g CH and about 25 mg to about 200 mg $AdSO_4$.

17. The method of claim 16, wherein (a) the concentration of the one or more cytokinins is:
 (i) about 4.64 µM KN;
 (ii) about 4.43 µM BA;
 (iii) about 4.54 µM TDZ;
 (iv) about 2.32 µM KN and about 2.21 µM BA;
 (v) about 2.21 µM BA and about 12.27 µM TDZ; or
 (vi) about 2.32 µM KN and about 2.27 µM TDZ; and (b) the amount of organic additive is:
 (i) about 1.0 g CH;
 (ii) about 100 mg $AdSO_4$; or
 (iii) about 1.0 g CH and about 100 mg $AdSO_4$.

18. The method of claim 12, wherein the media comprise:

first medium: MS basal medium and about 2.26 µM to about 9.04 µM 2,4-D; and second medium: MS basal medium, about 1.23 µM to about 4.92 µM IBA and about 0.72 µM to about 5.76 µM $GA_3$.

19. The method of claim 18, wherein the media comprise:

first medium: MS basal medium and about 6.78 µM 2,4-D; and second medium: MS basal medium, about 2.46 µM IBA and about 2.88 µM $GA_3$.

20. The method of claim 1, wherein each medium further comprises a source of carbon.

21. The method of claim 20, wherein the source of carbon is selected from the group consisting of sucrose, glucose, fructose, maltose, a mixture of sucrose and glucose, a mixture of fructose and glucose and a mixture of maltose and glucose.

22. The method of claim 21, wherein the source of carbon is selected from the group consisting of about 2% to about 5% sucrose, about 2% to about 5% glucose, about 2% to about 5% fructose, about 2% to about 5% maltose, a mixture of about 2% to about 3% sucrose and about 2% to about 3% glucose, a mixture of 1% to about 2% fructose and about 2% to about 3%, glucose and a mixture of 1% to about 2% maltose and about 2% to about 3% glucose.

23. The method of claim 1 which further comprises step (a1) after step (a) and before step (b) wherein step (a1) comprises treating the embryogenic callus with a mitotic inhibitor to induce chromosome doubling.

24. The method of claim 23, wherein the mitotic inhibitor is selected from the group consisting of colchicines and oryzalin.

25. The method of claim 23, wherein the embryogenic callus is treated with 0.1% to 0.5% of the mitotic inhibitor.

26. The method of claim 23, wherein the embryogenic callus is treated for one day to three days.

* * * * *